United States Patent [19]
Mandiberg

[11] Patent Number: 5,428,193
[45] Date of Patent: Jun. 27, 1995

[54] STETHOSCOPE COVER

[76] Inventor: Robert Mandiberg, 3822 Nairobi Pl., Oakland, Calif. 94605

[21] Appl. No.: 221,784

[22] Filed: Apr. 1, 1994

[51] Int. Cl.⁶ .......................... A61B 7/02; A61B 7/04; A61B 5/02
[52] U.S. Cl. ..................... 181/131; 128/715; 381/67
[58] Field of Search ............. 181/131, 137; 128/715, 128/773, 798, 639; 381/67

[56] References Cited

U.S. PATENT DOCUMENTS

| | | | |
|---|---|---|---|
| 1,344,655 | 6/1920 | Rubin | 181/137 |
| 1,410,034 | 3/1922 | Pollard | 181/137 |
| 1,425,158 | 8/1922 | Wolfsohn | 128/67 |
| 2,651,380 | 9/1953 | Brandenburg | 181/137 |
| 2,910,705 | 11/1959 | Coplan | 4/242 |
| 3,255,841 | 6/1966 | Hasbrouck | 181/131 |
| 4,401,125 | 8/1983 | Taylor et al. | 181/131 X |
| 4,461,368 | 7/1984 | Plourde | 181/131 |
| 4,871,046 | 10/1989 | Turner | 181/131 |
| 5,269,314 | 12/1993 | Kendall et al. | 128/715 |
| 5,365,023 | 11/1994 | Lawton | 181/131 |

*Primary Examiner*—Khanh Dang
*Attorney, Agent, or Firm*—Thomas R. Lampe

[57] ABSTRACT

A removable cover for temporarily covering the diaphragm portion of a stethoscope is of integral, molded, one-piece construction and wholly formed of flexible, resilient, imperforate material. The cover includes a thin, flexible, liquid impervious, void-free planar wall larger than the diaphragm portion opening and a flexible, liquid impervious, void-free side wall extending from the planar wall which fits snugly over the tapered wall of the diaphragm portion.

3 Claims, 1 Drawing Sheet

STETHOSCOPE COVER

TECHNICAL FIELD

This invention relates to a cover for covering the diaphragm portion of a stethoscope. More particularly, the cover is for the purpose of protecting the diaphragm portion from contamination. The cover is readily applied to and removed from the diaphragm portion or head of a stethoscope.

It is recognized that stethoscopes can become soiled and contaminated during use and may, in turn, transfer contamination from one patient to another. Recognizing the existence of this problem, a number of cover arrangements have been devised and are disclosed in the prior art for covering all or a portion of the diaphragm or head portion of a stethoscope.

U.S. Pat. No. 5,369,314, issued Dec. 14, 1993, discloses a disposable fabric cover temporarily held in position over a stethoscope head by an elastic strap or band. By definition, a fabric material is somewhat porous and will not provide an effective means for avoiding contamination of a stethoscope head. Furthermore, such a construction is relatively expensive, employing several structural components which must be assembled during manufacture.

U.S. Pat. No. 4,461,368, issued Jul. 24, 1984, discloses a stethoscope cover having a flexible membrane of latex and a rigid rim member. Such an arrangement is relatively complex and expensive and does not particularly lend itself to disposal and replacement after a single use.

U.S. Pat. No. 4,871,046, issued Oct. 3, 1989, discloses a disposable shield for stethoscope heads in the form of an envelope which is formed from a single piece of plastic material in which the sides are folded toward each other, thereby defining two top portions overlaying a bottom portion. The edges are sealed as by heat sealing. In a preferred embodiment, the shields are formed and connected together in a ribbon or roll. Through the use of perforations, adjoining shields may be disconnected from one another during dispensing. While this arrangement has the characteristics of relative simplicity and low cost, the envelopes, being of a rectangular configuration, do not provide an effective seal over the stethoscope head. Furthermore, the arrangement will allow relative freedom of movement between the cover and the stethoscope head during use, a situation that is not desirable when one wishes to avoid contamination of the head.

A search of the prior art also located the following United States patents: U.S. Pat. No. 2,910,705, issued Nov. 3, 1959, U.S. Pat. No. 2,651,380, issued Sep. 8, 1953, U.S. Pat. No. 1,425,158, issued Aug. 8, 1922, U.S. Pat. No. 1,410,034, issued Mar. 21, 1922, U.S. Pat. No. 1,344,655, issued Jun. 29, 1920, and U.S. Pat. No. 3,255,841, issued Jun. 14, 1966.

DISCLOSURE OF INVENTION

The present invention relates to a stethoscope cover which is highly effective for preventing contamination of a stethoscope head or diaphragm portion. The cover is characterized by its relative simplicity and low cost, making it particularly suitable for use as an item which can be employed only for a single patient and then readily disposed of and replaced for use when applying a stethoscope to another patient. In addition, the cover, while remaining securely in place during use, can be readily applied to a stethoscope head or removed therefrom in an instant.

The removable cover of the present invention is for temporarily covering the diaphragm portion of a stethoscope, the diaphragm portion including a rigid cup-shaped member having an enlarged end defining an opening accommodating a diaphragm and a reduced end spaced from the diaphragm. The rigid cup-shaped member has a tapered outer wall extending between the enlarged end and the reduced end.

The removable cover is of integral, molded, one-piece construction and wholly formed of flexible, resilient, imperforate material.

The cover has a thin, flexible, liquid impervious, void-free planar wall larger than the diaphragm portion opening.

The cover further includes a flexible, liquid impervious, void-free side wall extending outwardly from the outer periphery of the planar wall, the side wall tapering inwardly in the direction away from the planar wall and terminating at a side wall edge defining a cover opening.

The planar wall and the side wall define an interior for receiving and accommodating therein the diaphragm portion of a stethoscope with the side wall in snug engagement with the tapered outer wall of the diaphragm portion about the entire circumference of the tapered outer wall and the planar wall disposed completely over the diaphragm.

The cover opening is substantially smaller than the enlarged end of the rigid cup-shaped member and the side wall edge at the cover opening deformable to allow passage of the enlarged end therethrough when applying the cover to a stethoscope or removing the cover from a stethoscope.

Other features, advantages, and objects of the present invention will become apparent with reference to the following description and accompanying drawings.

BEST MODE FOR CARRYING OUT THE INVENTION

Figure 1:
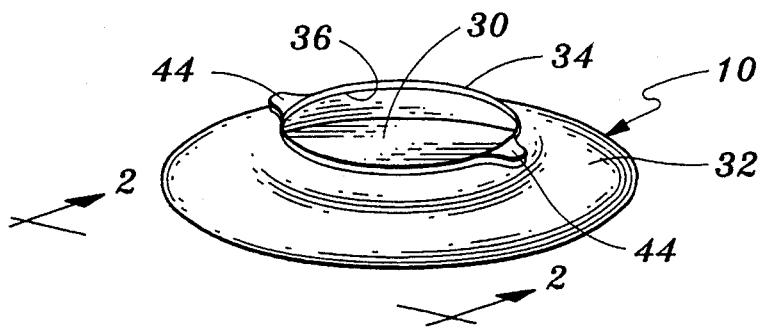
FIG. 1 is a perspective view of a removable cover constructed in accordance with the teachings of the present invention.
Figure 2:
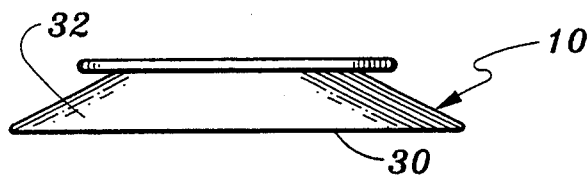
FIG. 2 is a front, elevation view in the direction of arrows 2—2 in FIG. 1.

Referring now to the drawings, a removable cover constructed in accordance with the teachings of the present invention is designated by reference numeral 10. Cover 10 is for placement over the head or diaphragm portion 12 of a stethoscope. The diaphragm portion includes a rigid cup-shaped member 14 having an enlarged end 16 defining an opening 17 (shown by dash lines in FIG. 3) accommodating a diaphragm (not shown) and a reduced end 18 spaced from the diaphragm. As is also conventional, rigid cup-shaped member 14 has a tapered outer wall 20 extending between the enlarged end and reduced end.

Cover 10 is of integral, molded, one-piece construction and wholly formed of flexible, resilient, imperforate material. One highly suitable material is molded latex.

The cover 10 has a thin, flexible, liquid impervious, void-free planar wall larger than the diaphragm portion opening.

The cover also includes a flexible, liquid impervious, void-free side wall 32 extending outwardly from the outer periphery of the planar wall. The side wall tapers inwardly in the direction away from the planar wall and terminates at a side wall edge 34 defining a cover opening 36.

Figure 5:
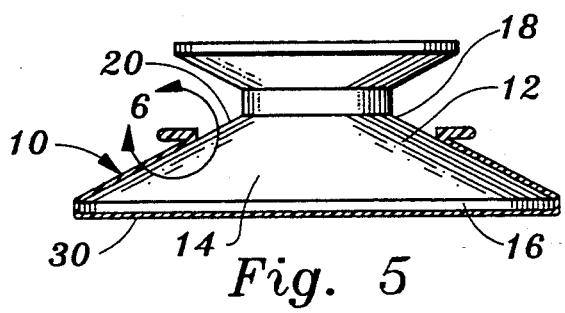
FIG. 5 is an enlarged, cross-sectional view taken along the line 5—5 in FIG. 4.

The planar wall 30 and the side wall 32 define an interior for receiving and accommodating therein the head or diaphragm portion 12 of a stethoscope. This can perhaps best be seen with reference to FIG. 5. When the cover is in place on the diaphragm portion, the side wall 32 is in snug engagement with the tapered outer wall of the diaphragm portion about the entire circumference of the tapered outer wall. Also, the planar wall 30 is completely over the diaphragm itself.

Cover opening 36 is substantially smaller than the enlarged end 16 of the rigid cup-shaped member 14. The side wall edge at the cover opening is deformable to allow passage of the enlarged end therethrough when applying the cover to a stethoscope or when removing the cover from a stethoscope.

Figure 3:
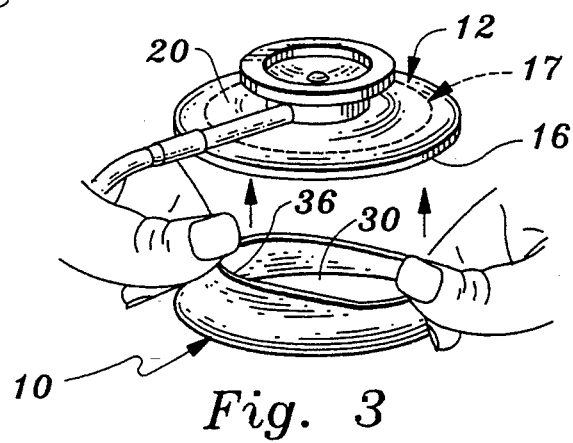
FIG. 3 is a perspective view illustrating the cover being applied to the diaphragm portion of a stethoscope.
Figure 4:
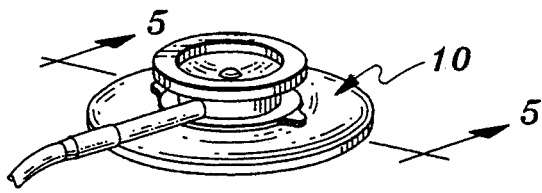
FIG. 4 illustrates the cover in place on the diaphragm portion of a stethoscope.

It should be noted that the tapered side wall 32 increases in thickness at the side wall edge to form a reinforcement lip 40 surrounding the cover opening. This will resist tearing or ripping of the cover when it is stretched to be positioned over the diaphragm portion of the stethoscope as shown in FIG. 3.

Figure 6:
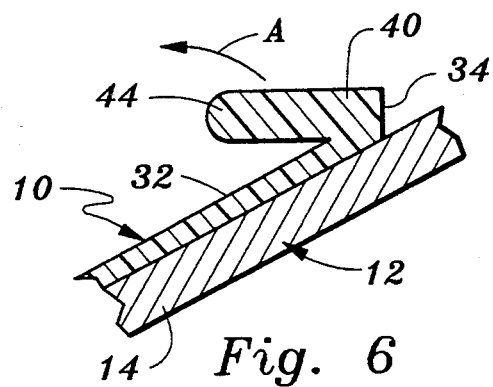
FIG. 6 is a greatly enlarged, detail view of that portion delineated in FIG. 5 by double headed arrow 6.

To facilitate application of the cover to the stethoscope head as well as to facilitate removal of the cover therefrom, it is desirable to mold the cover with two integral tabs 44 which may be grasped and pulled to manipulate the cover for placement or removal. FIG. 6 illustrates a tab 44 having force applied thereto in the direction of arrow A to pull the lip away from the tapered outer wall 20.

When practicing the present invention it is desirable to restrict the thickness of planar wall 30 to no more than 0.75 mm when the cover is formed of latex so as not to interfere with the sound transmission of the stethoscope. While it is preferred that the planar wall 30 be relatively taut over the opening of the diaphragm portion, it has been found that the planar wall will still allow for the proper transmission of sound energy even when it is relatively loose at the opening since pressure of the stethoscope head against the patient's skin will in itself tend to make the planar wall somewhat taut.

I claim:

1. Apparatus including a removable cover for temporarily covering the diaphragm portion of a stethoscope, said diaphragm portion being of fixed size and configuration and including a rigid cup-shaped member having an enlarged end with a circular-shaped outer peripheral rim defining an opening accommodating a diaphragm and a reduced end spaced from said diaphragm, said rigid cup-shaped member having a tapered outer wall extending from said circular-shaped outer peripheral rim between said enlarged end and said reduced end, said removable cover being of integral, molded, one-piece construction and wholly formed of flexible, resilient, imperforate material, said removable cover having a thin, flexible, liquid impervious, void-free, circular-shaped planar wall larger than the diaphragm portion opening and a flexible, liquid impervious, void-free side wall extending completely about and away from the outer periphery of said planar wall, said side wall tapering inwardly in a direction away from said planar wall and terminating at a side wall edge defining a centrally disposed, circular-shaped cover opening spaced from and substantially co-axial with the outer periphery of said planar wall, said cover opening comprising the sole opening in said removable cover, said planar wall and said side wall when in an unstretched condition defining an interior smaller than said rigid cup-shaped member for receiving and accommodating therein the diaphragm portion of a stethoscope whereby said side wall will be in snug engagement with the tapered outer wall of the diaphragm portion about the entire circumference of the tapered outer wall when said rigid cup-shaped member is accommodated in said interior, and the planar wall disposed completely over the diaphragm and extending in a plane defined by said circular-shaped outer peripheral rim when said rigid cup-shaped member is accommodated in said interior, said cover opening being substantially smaller than the enlarged end of said rigid cup-shaped member and said side wall edge at said cover opening being deformable upon application of external forces thereto to stretch and allow passage of the enlarged end therethrough when applying the cover to a stethoscope or when removing the cover from a stethoscope, said tapered side wall increasing in thickness at said side wall edge to form a reinforcement lip surrounding said cover opening, and at least one manually graspable member attached to the cover for facilitating placement of the cover on a stethoscope diaphragm portion and removal of said cover therefrom, said manually graspable member being attached to said reinforcement lip and projecting outwardly away from said cover opening.

2. The removable cover according to claim 1 wherein said flexible, resilient, imperforate material is molded latex.

3. Apparatus including a removable cover for temporarily covering the diaphragm portion of a stethoscope, said diaphragm portion being of fixed size and configuration and including a rigid cup-shaped member having an enlarged end with a circular-shaped outer peripheral rim defining an opening accommodating a diaphragm and a reduced end spaced from said diaphragm, said rigid cup-shaped member having a tapered outer wall extending from said circular-shaped outer peripheral rim between said enlarged end and said reduced end, said removable cover being of integral, molded, one-piece construction and wholly formed of flexible, resilient, imperforate material, said removable cover having a thin, flexible, liquid impervious, void-free, circular-shaped planar wall larger than the diaphragm portion opening and a flexible, liquid impervious, void-free side wall extending completely about and away from the outer periphery of said planar wall, said side wall tapering inwardly in a direction away from said planar wall and terminating at a side wall edge defining a centrally disposed, circular-shaped cover opening spaced from and substantially co-axial with the outer periphery of said planar wall, said cover opening comprising the sole opening in said removable cover, said planar wall and said side wall when in an unstretched condition defining an interior smaller than said rigid cup-shaped member for receiving and accommodating therein the diaphragm portion of a stethoscope whereby said side wall will be in snug engagement with the tapered outer wall of the diaphragm portion about the entire circumference of the tapered outer wall when said rigid cup-shaped member is accommodated in said interior, and the planar wall disposed completely over the diaphragm and extending in a plane defined by said circular-shaped outer peripheral rim when said rigid cup-shaped member is accommodated in said interior, said cover opening being substantially smaller than the enlarged end of said rigid cup-shaped member and said side wall edge at said cover opening being deformable upon application of external forces thereto to stretch and allow passage of the enlarged end therethrough when applying the cover to a stethoscope or when removing the cover from a stethoscope, said tapered side wall increasing in thickness at said side wall edge to form a reinforcement lip surrounding said cover opening, and a pair of manually graspable tabs attached to said reinforcement lip at spaced locations on said reinforcement lip and projecting away from said cover opening, said manually graspable tabs for selectively facilitating placement of the cover on a stethoscope diaphragm portion or facilitating removal of the cover from a stethoscope diaphragm portion.

* * * * *